United States Patent [19]

Ager

[11] Patent Number: 5,128,497
[45] Date of Patent: Jul. 7, 1992

[54] CONVERSION OF PYRETHROID ISOMERS TO MORE ACTIVE SPECIES

[75] Inventor: John W. Ager, Princeton, N.J.

[73] Assignee: FMC Corporation, Philadelphia, Pa.

[21] Appl. No.: 460,445

[22] Filed: Jan. 3, 1990

[51] Int. Cl.$^5$ .................. C07C 253/34; C07C 69/743; C07C 69/747

[52] U.S. Cl. .................................... 558/354; 558/407; 560/124

[58] Field of Search ................. 558/354, 407; 560/124

[56] References Cited

U.S. PATENT DOCUMENTS

| | | | |
|---|---|---|---|
| 4,213,916 | 7/1980 | Davies et al. | 260/465 |
| 4,308,279 | 12/1981 | Smeltz | 424/304 |
| 4,427,598 | 1/1984 | Mason et al. | 260/465 |
| 4,512,931 | 4/1985 | Robson | 260/465 |
| 4,544,508 | 10/1985 | Fuchs et al. | 260/465 |
| 4,544,510 | 10/1985 | van Berkel et al. | 260/465 |
| 4,656,303 | 4/1987 | Kurono et al. | 558/354 |
| 4,670,464 | 6/1987 | Doyle et al. | 514/521 |
| 4,681,969 | 7/1987 | Williams et al. | 558/407 |
| 4,733,001 | 3/1988 | Suzki et al. | 558/354 |
| 4,782,174 | 11/1988 | Fuchs et al. | 558/354 |
| 4,845,126 | 7/1989 | Hidasi et al. | 514/521 |

FOREIGN PATENT DOCUMENTS

| | | |
|---|---|---|
| 8604215 | 7/1986 | PCT Int'l Appl. . |
| 8604216 | 7/1986 | PCT Int'l Appl. . |
| 8810249 | 12/1988 | PCT Int'l Appl. . |
| 2064528 | 6/1981 | United Kingdom . |

*Primary Examiner*—Joseph Paul Brust
*Attorney, Agent, or Firm*—Stanford M. Back; H. Robinson Ertelt; Robert M. Kennedy

[57] ABSTRACT

Crystalline pyrethroid isomers or enantiomer pairs are converted to more pesticidally active isomers by contacting a hydrocarbon slurry of the starting isomers with an epimerization agent selected from the group consisting of 1,1,3,3-tetramethylguanidine and 1,8-diazabicyclo[5.4.0]undec-7-ene, agitating the slurry while maintaining a temperature effective for conversion, and recovering the resulting isomers. The process typically is effective for enriching cypermethrin, and cyfluthrin.

8 Claims, No Drawings

CONVERSION OF PYRETHROID ISOMERS TO MORE ACTIVE SPECIES

TECHNICAL FIELD

This invention relates to the transformation of pesticidally less active pyrethroid isomers into isomers which are more pesticidally active than the starting isomers.

BACKGROUND OF THE INVENTION

The pyrethroids with which the present invention is concerned are crystallizable esters having at least one asymmetric carbon atom to which an epimerizable proton is attached. These pesticidally active pyrethroids additionally contain at least one and usually two or more other asymmetric carbon atoms and therefore comprise isomeric mixtures wherein one or more of the isomers are more pesticidally active than the others. Representative of such pyrethroids are the alpha-cyanobenzyl esters of the formula (A):

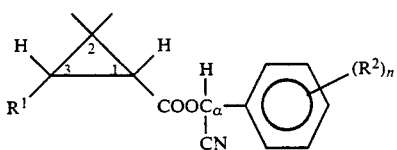

A wherein $R^1$ is halogen, haloalkyl, alkenyl or haloalkenyl; each $R^2$ independently is halogen, alkyl, haloalkyl, alkoxy, phenyl, phenoxy, phenylalkyl, substituted phenyl and substituted phenylalkyl wherein the substituents include one or more of alkyl, halogen, haloalkyl, nitro, hydroxy and cyano; and n is 0-5, preferably 1-3. In the above formula the asymmetric carbon atoms are marked 1, 3 and alpha ($\alpha$). All of the substituents on a host group may be the same, or the substituents may be different. Alkyl and alkoxy may contain 1-8 carbon atoms, preferably 1-4 carbon atoms. Alkenyl may comprise 2-8 carbon atoms, preferably 2-4 carbon atoms. Halogen includes fluorine, chlorine and bromine. A typical phenylalkyl group is benzyl. Substituted phenyl includes tolyl, xylyl, trichlorophenyl and trifluoromethylphenyl. Substituted phenylalkyl includes methylbenzyl, trichlorobenzyl and trifluoromethylbenzyl.

The foregoing and other pyrethroids are well known as disclosed, for example, in Kirk-Othmer, Encyclopedia of Chemical Technology, Second Edition, Vol. 13, pages 456-458, in the following U.S. Pat. Nos:

4,024,163—Elliot et al (NRDC)
4,133,826—Warnant et al (Roussel Uclaf)
4,136,195—Warnant et al (Roussel Uclaf)
4,213,916—Davies et al (Shell)
4,287,208—Fuchs et al (Bayer)
4,308,279—Smeltz (FMC)
4,427,598—Mason et al (Shell)
4,512,931—Robson (ICI)
4,544,508—Fuchs et al (Bayer)
4,544,510—Van Berkel et al (Shell)
4,560,515—Stoutamire et al (Shell)
4,582,646—Stoutamire et al (Shell)
4,670,464—Doyle et al (ICI)
4,681,969—Williams et al (ICI)

and in the following PCT patent publications:

WO 86/04215—Hidasi et al (Chinoin)
WO 86/04216—Hidasi et al (Chinoin)

All of the listed patents and publications are incorporated herein by reference.

Preferred pyrethroids convertible to more active isomers in accordance with the present invention are those of formula A wherein $R^1$ is dihalovinyl or a tetrahalopropenyl group such as 3,3,3-trifluoro-2-chloropropen-1-yl, $R^2$ is phenoxy, and n is 1 or 2. The more preferred pyrethroids are those wherein n is 1, $R^1$ is dihalovinyl or tetrahalopropenyl and $R^2$ is phenoxy; and those wherein n is 2, $R^1$ is dihalovinyl or tetrahalopropenyl and one $R^2$ is fluorine and the other $R^2$ is phenoxy. The preferred compounds are isomeric mixtures having the common name "cyfluthrin" when $R^1$ is dichlorovinyl, n is 2 and one $R^2$ is 4-fluoro and the other $R^2$ is 3-phenoxy. When $R^1$ is dichlorovinyl, n is 1 and $R^2$ is phenoxy, the preferred mixtures have the common name "cypermethrin."

Cypermethrin contains four cis and four trans isomers designated I-VIII as follows:

cis isomers

I. (S) ($\alpha$-cyano) (3-phenoxyphenyl)methyl 1R, cis-3-(2,2-dichloroethenyl)-2,2-dimethylcyclopropanecarboxylate (abbreviated 1R, cis S)cis S)
II. (R) ($\alpha$-cyano) (3-phenoxyphenyl)methyl 1S,cis-3-(2,2-dichloroethenyl)-2,2-dimethylcyclopropanecarboxylate (abbreviated 1S,cis R)
III. (S) ($\alpha$-cyano) (3-phenoxyphenyl)methyl 1S,cis-3-(2,2-dichloroethenyl)-2,2-dimethylcyclopropanecarboxylate (abbreviated 1S,cis S)
IV. (R) ($\alpha$-cyano) (3-phenoxyphenyl)methyl 1R,cis-3-(2,2-dichloroethenyl)-2,2-dimethylcyclopropanecarboxylate (abbreviated 1R,cis R)

trans isomers

V. The trans isomer of I (abbreviated 1R, trans S)
VI. The trans isomer of II (abbreviated 1S,trans R)
VII. The trans isomer of III (abbreviated 1S,trans S)
VIII. The trans isomer of IV (abbreviated 1R,trans R)

Cyfluthrin and other pyrethroids to which the invention is applicable comprise similar isomeric mixtures.

It is known that the most insecticidally active isomers of the foregoing eight isomers are I and V, and that enantiomer pairs I/II (abbreviated cis-2) and V/VI (abbreviated trans-2) are more insecticidally active than the enantiomer pairs III/IV (abbreviated cis-1) and VII/VIII (abbreviated trans-1). It is extremely difficult and commercially impractical to separate the more active isomers such as I and V from the complex isomer mixtures produced in the usual pyrethroid synthesis. Accordingly, efforts to produce more pesticidally active pyrethroids have focused on techniques for converting less active isomers in the synthesis product mixtures to more active isomers, i.e., to enrich isomeric mixtures with respect to the more active isomers, thus avoiding complex resolution procedures and the loss represented by discard of less active isomers.

Nevertheless, even when the isomeric mixtures have been converted rather than resolved, the conversion procedures have not been commercially practical because of poor yields, usually due to production of undesired by-product, often comprising as many isomers as the desired product, and because of time-consuming multiple steps, high temperatures and/or the need to recover expensive reagents. In the case of cypermethrin the major by-product is (R,S)-2-oxo-1,2-bis(3-phenoxyphenyl) ethyl cis- and trans-3-(2,2-dichloroethenyl)-2,2-dimethylcyclopropanecarboxylate, an eight isomer mixture commonly called the "benzoin by-product." Similar by-products are encountered in the synthesis of other pyrethroids such as cyfluthrin. Representative of prior efforts to convert isomer mixtures to more active species are the procedures disclosed in U.S. Pat. Nos. 4,213,916, 4,308,279, 4,544,510, 4,544,508, 4,512,931, 4,427,598, 4,670,646 and 4,681,969, the two PCT patent publications cited above, and the process disclosed in my prior application, U.S. Ser. No. 197,725 filed May 23, 1988 now U.S. Pat. No. 4,997,970.

SUMMARY OF THE INVENTION

It has now been found, that pesticidally less active pyrethroid isomers can be converted to the desired, more pesticidally active, isomers by incorporating into a reaction mixture a hydrocarbon solvent, the starting pesticidally less active pyrethroid isomer or mixture thereof; and an epimerization agent selected from the group consisting of 1,1,3,3-tetramethylguanidine and 1,8-diazabicyclo-[5.4.0]undec-7-ene; agitating the resulting slurry at a temperature effective for conversion, and recovering the resulting crystallized, more active isomers.

In one aspect of the invention, single less active isomers are converted by the treatment to single more active isomers, or less active diastereomer mixtures are converted to single more active isomers, or a starting mixture of more active and less active enantiomer pairs is converted to an enantiomer pair mixture enriched, i.e., predominating, in the more active enantiomer pairs.

In another aspect of the invention the starting isomeric mixture is a mixture of all of the enantiomer pairs of cypermethrin or cyfluthrin, single pairs thereof, or any combination of the pairs, such as the cis-1 and cis-2 pairs and/or the trans-1 and trans-2 pairs, and the product mixture contains higher proportions of the more active enantiomer pairs.

By the process of the invention pesticidally inactive or less active isomers or enantiomers are converted to active or more active isomers or enantiomers, and mixtures of both the more active and less active isomers or enantiomers are enriched in the more active isomers or enantiomers.

The process is effective at room temperature range and with solvents which are usable in the preceding esterification reaction in which the pyrethroids are formed, thus presenting opportunity for avoiding solvent exchange. Moreover, the reagents for the conversion are inexpensive and by-product is substantially reduced with concomitant increased yield of more active product. The process therefore is eminently suitable for commercial production.

DETAILED DESCRIPTION

While the following description emphasizes application of the invention to isomers of cypermethrin and cyfluthrin, it will be understood that the invention is applicable to any crystallizable pyrethroid isomer or isomeric mixture, that is, to crystallizable pyrethroid compounds having at least one asymmetric carbon atom carrying an epimerizable proton. However, the invention is especially adapted to treatment of crystallizable pyrethroids having an epimerizable proton on an asymmetric carbon atom bearing a cyano group and a plurality of asymmetric carbon atoms. Such pyrethroids normally comprise mixtures of numerous isomers including enantiomer pairs, such as the eight isomers (four enantiomer pairs) of cypermethrin and cyfluthrin, described above. As pointed out above, the more isomers a pyrethroid comprises, the more difficult and expensive it is to produce the more active isomers or mixtures enriched therein. In this specification, "isomers" means and includes enantiomer pairs as well as individual isomers and isomer mixtures.

Accordingly, the starting material of the invention may be either a crude material, such as an unpurified reaction mixture containing crystallizable pyrethroid isomers, or the starting material may be purified so that it contains known isomers and proportions thereof.

While the starting material initially may be in the liquid state it is necessary for the success of the invention that crystallization be initiated in a liquid medium so that the material is in a slurry form during the reaction with the epimerization agent. Thus the starting material may either be totally solid or may be a liquid mixture in which crystallization is induced by seeding with one or more crystals of the more active isomers it is desired to produce. Preferably, the starting material is totally solid.

The liquid medium in which the reaction mixture is formed consists essentially of an inert, nonpolar, hydrocarbon solvent in which the desired isomers are substantially insoluble and the less pesticidally active isomers are relatively more soluble. Such inert hydrocarbons include aliphatic or cycloaliphatic hydrocarbons which are liquids in an ambient temperature range for plant processes, e.g., about 5°-35° C., preferably 10°-25° C. Generally, the hydrocarbons contain about 5-16 carbon atoms, preferably 6-8 carbon atoms, and therefore include straight chain and branched pentanes, hexanes, heptanes, octanes, the cyclic counterparts thereof, and any mixtures thereof.

Other solvents may be used with the hydrocarbons in the liquid medium provided they are not present in such amounts as will reduce or destroy the effectiveness of the treatment. For example, while some water or a polar organic liquid such as acetonitrile may be present in the liquid medium, it has been determined that polar liquids tend to inhibit the process by rendering the pyrethroids more soluble and thus reduce the yields of the desired more active isomers. Water in major amounts is also undersirable because it decreases yield by increasing by-product. Likewise, the hydrocarbon solvent may include minor amounts of aromatic hydrocarbon components; again such components reduce the yield of useful product, principally by increasing solubility, thereby inhibiting crystallization. The liquid medium of the slurry therefore must predominately comprise an inert hydrocarbon solvent selected for substantial insolubility of the desired isomers therein.

The solvent is used in an amount which provides a fluid medium for the conversion process and such that the medium can be agitated easily. About 1-10 parts by weight of solvent per part by weight of pyrethroid starting material usually will be sufficient but the amount may be varied depending upon the starting material. A preferred proportion is about 2-4 parts by weight of solvent per part by weight of pyrethroid. More preferably the amount of hydrocarbon solvent is such that the reaction mixture is initially or becomes substantially saturated with the desired isomers. Most preferably the amount is such that the starting mixture is a readily stirrable slurry.

The process of this invention is carried out in the presence of an epimerization agent selected from 1,1,3,3-tetramethylguanidine and 1,8-diazabicyclo-

[5.4.0]undec-7-ene, which agents may be used singly or in any mixture of the two.

The epimerization agents preferably are added to the hydrocarbon solvent medium as solids. The amount of epimerization agent may be varied depending on the economics of the treatment, e.g., residence time of the process. Lower concentrations may require longer treatment time than stronger concentrations. Typically, the epimerization agent is used in amounts of about 0.5 percent to about 5.0 percent by weight of pyrethroid starting material, with 1 percent to 2 percent by weight of pyrethroid being preferred.

It is a particular advantage of the present invention that it is not necessary or desirable to utilize catalysts heretofore employed in epimerizing pyrethroids, thereby eliminating an essential and costly reactant from the process of my prior application U.S. Ser. No. 197,725, above.

The reaction mixture, a slurry containing pyrethroid isomers, solvent and epimerization agent is agitated for such time and at such temperature as necessary to induce conversion to the desired isomers. One of the advantages of the invention is that the conversion may be carried out at conventional ambient temperature conditions such as about 5°–35° C., preferably about 10°–25° C. Typically, the reaction mixture is agitated for about 2 to about 24 hours, preferably about 3 to 8 hours.

The products may then be recovered by any conventional means, for example by neutralizing or inactivating the epimerization agent with an acid, extracting the reaction mixture, then stripping the solvent from the extract. The product may also be recovered by filtration, evaporation, decantation, centrifugation or any combination thereof. Although the reaction mixture can be cooled prior to filtration, it is preferred that the temperature be maintained throughout the process to reduce the possibility of trapping undesired impurities in the crystalline structure of the product. If desired, the product may be recrystallized one or more times to upgrade purity.

The hydrocarbon solvent is believed to be critical to the success of the process because it has been found that the more active isomers are less soluble therein than are the less active isomers. At equilibrium, therefore, formation of the more active isomers is favored and is further promoted by removal of the solid, more active species as it is formed. Accordingly, by using a hydrocarbon as the dominant solvent in the process, the reaction is driven to produce the more active cis-2 pair at the expense of the less active cis-1 pair. Similar principles are believed applicable to other isomer mixtures, for example, the conversion of the less active trans-1 pair to the more active trans-2 pair.

The following examples further illustrate the invention. In the examples, the terms cis, trans, cis-1, cis-2, trans-1 and trans-2 refer to the isomers and enantiomer pairs of cypermethrin as defined above and as the case may be. In each case the compound name followed by the liquid chromatograph analysis (% area) is further abbreviated as follows: $C_1$ = cis-1 enantiomer pair; $C_2$ = cis-2 enantiomer pair; $T_1$ = trans-1 enantiomer pair; $T_2$ = trans-2 enantiomer pair; $B_1$ = cis-1 benzoin by-product enantiomer pair; $B_2$ = cis-2 benzoin by-product enantiomer pair; $B_3$ = trans-1 by-product benzoin enantiomer pair; and $B_4$ = trans-2 by-product benzoin enantiomer pair.

Example 1 illustrates the enrichment process of the present invention, in which the epimerization is neutralized or inactivated, then toluene is used to extract the resulting isomer mixture in its entirety. The enriched isomers may then be obtained as a solid by evaporating or stripping the toluene from the toluene extract.

EXAMPLE 1

Preparation of a Mixture of the Isomers (S)-(Cyano)-(3-Phenoxyphenyl) Methyl (1R, cis)-3-(2,2-Dichloroethenyl)-2,2-Dimethylcyclopropanecarboxylate and (R)-(Cyano)-(3-Phenoxyphenyl)-Methyl (1S,cis)-3-(2,2-Dichloroethenyl)-2,2-Dimethylcyclopropanecarboxylate A mixture of 5.0 grams (0.012 mole) of (R,S)-(cyano)-(3-phenoxyphenyl)methyl cis-3-(2,2-dichloroethenyl)-2,2-di-methylcyclopropanecarboxylate ($C_1 = 52.7$, $C_2 = 41.2$, $T_1 = 2.7$, $T_2 = 1.2$), 10.0 grams of n-heptane, and 0.05 gram (0.00043 mole) of 1,1,3,3-tetramethylguanidine was stirred at room temperature for 17.25 hours. Dilute hydrochloric acid was added, and the mixture was extracted with toluene. The organic phase was analyzed by liquid chromatography and found to contain the cis-2 enantiomer pair of (R,S)-(cyano) (3-phenoxyphenyl)methyl cis-3-(2,2-dichloroethenyl)-2,2-dimethylcyclopropanecarboxylate ($C_1 = 7.0$, $C_2 = 89.0$, $T_1 = 0.9$, $T_2 = 1.3$, $B_1 = 0.6$, $B_2 = 0.5$).

Tables 1 and 2 set forth additional examples of the reaction as generally described above. Table 1 summarizes runs with cis-cypermethrin. While a starting material containing 41.2 wt % of the $C_2$ isomers was used in the example, it will be apparent that a wide range of isomer mixes may be employed, for example mixes containing from about 10 wt % to about 60 wt % of the starting mixture, and that the product may be enriched in the desired isomer by 15 to about 120 percent. Table 2 illustrates runs using cis-trans cypermethrin in which a similar enrichment is seen in the desired cis and trans isomers.

Examples 2 and 3 illustrate an embodiment of the invention in which the enriched isomer mixture is recovered by filtration.

EXAMPLE 2

Preparation of a Mixture of the cis-2 and trans-2 Enantiomer Pairs of (Cyano) (3-Phenoxyphenyl) Methyl cis, trans-3-(2,2-Dichloroethenyl)-2,2-Dimethylcyclopropanecarboxylate A stirred slurry of 10.0 grams of (R,S)-(cyano)(3-phenoxyphenyl)methyl cis,trans-3-(2,2-dichloroethyenyl)-2,2-dimethylcyclopropanecarboxylate ($C_1 = 27.4$, $C_2 = 27.8$, $T_1 = 22.6$, and $T_2 = 20.0$) and 0.1 gram of 1,1,3,3-tetramethylguanidine in 20.0 grams of n-heptane was stirred at room temperature for 20.5 hours. The reaction mixture was cooled to 5° C. for 30 minutes. Ten milliliters of cold, 1N hydrochloric acid was added. This mixture was stirred for 15 minutes and was filtered. The filter cake was washed with 5 mL of fresh n-heptane and was dried under reduced pressure to yield 8.78 grams of the cis-2 and trans-2 enantiomer pairs of (R,S)-(cyano) (3-phenoxyphenyl)methyl cis,-trans-3-(2,2-dichloroethenyl)-2,2-dimethylcyclopropanecarboxylate ($C_1 = 2.4$, $C_2 = 47.5$, $T_1 = 1.3$, and $T_2 = 48.8$).

This reaction was repeated exactly as above using 10.0 grams of a starting material with the following analysis: $C_1=27.4$, $C_2=23.3$, $T_1=28.2$, and $T_2=21.1$. The product analysis was: 8.61 grams, $C_1=2.3$, $C_2=47.0$, $T_1=1.4$, and $T_2=49.3$.

EXAMPLE 3

Preparation of the cis-2 Enantiomer Pair of (R,S)-(Cyano) (3-Phenoxyphenyl) Methyl cis-3-(2,2-Dichloroethenyl)-2,2-Dimethylcyclopropanecarboxylate A stirred slurry of 10.0 grams of (R,S)-(cyano) (3-phenoxyphenyl)methyl cis-3-(2,2-dichloroethenyl)-2,2-dimethylcyclcopropanecarboxylate ($C_1=52.5$, $C_2=45.0$) and 0.1 gram of 1,1,3,3-tetramethylguanidine in 20.0 grams of n-heptane was stirred at room temperature for 21 hours. The reaction mixture was cooled to 5° C. for 30 minutes. Ten milliliters of cold, 1N hydrochloric acid was added. This mixture was stirred for 15 minutes and was filtered. The filter cake was washed with 5 mL of fresh n-heptane and was dried under reduced pressure to yield 9.23 grams of the cis-2 enantiomer pair of (R,S)-(cyano) (3-phenoxyphenyl)methyl cis-3-(2,2-dichloroethenyl)-2,2-dimethylcyclopropanecarboxylate ($C_1=5.65$, $C_2=88.3$).

This reaction was repeated exactly as described above to yield 9.14 grams of the cis-2 enantiomer pair ($C_1=5.7$, $C_2=90.1$).

Example 4 illustrates the use of 1,8-diazabicyclo[5.4.0]undec-7-ene as the epimerization agent.

EXAMPLE 4

Preparation of the cis-2 Enantiomer Pair of (R,S)-(Cyano) (3-Phenoxyphenyl) Methyl cis-3-(2,2-Dichloroethenyl)-2,2-Dimethylcyclopropanecarboxylate A stirred slurry of 5.0 grams (0.012 mole) of (R,S)-(cyano) (3-phenoxyphenyl)methyl cis-3-(2,2-dichloroethenyl)-2,2-dimethylcyclopropanecarboxylate ($C_1=52.5$, $C_2=45.0$) and 0.2 gram (0.0013 mole) of 1,8-diazabicyclo[5.4.0]undec-7-ene in 10.0 grams of n-heptane was stirred at room temperature for 2.0 hours. Dilute hydrochloric acid was then added, and the mixture was extracted with toluene. The organic phase was analyzed by liquid chromatography and found to contain primarily the cis-2 enantiomer pair of (R,S)-(cyano) (3-phenoxyphenyl)methyl cis-3-(2,2-dichloroethenyl)-2,2-dimethylcyclopropanecarboxylate ($C_1=10.8$, $C_2=83.0$, $T_1=1.0$, $T_2=1.3$, $B_1=1.3$, and $B_2=1.0$).

TABLE 1

Enantiomeric Enrichment of cis-Cypermethrin Using 1,1,3,3-Tetramethylguanidine (TMG) in n-Heptane (solvent) at Room Temperature

| Experiment No. | TMG Amount (g) | Solvent Amount (g) | Reaction Time (Hr) | Starting Material[a] (g) | Product Analysis Liquid Chromatography-Area % | | | | | |
|---|---|---|---|---|---|---|---|---|---|---|
| | | | | | C1 | C2 | T1 | T2 | B2 | B2 |
| 1 | 0.01 | 10.0 | 17.25 | 5.0 | 45.0 | 53.0 | 1.1 | 1.0 | 0.6 | NR |
| 2 | 0.024 | 10.0 | 17.25 | 5.0 | 17.0 | 80.0 | 0.7 | 1.2 | 0.3 | 0.2 |
| 3 | 0.05 | 20.0 | 25.5 | 10.0 | 38.0 | 59.0 | 1.4 | 1.0 | 01 | 0.1 |
| 4 | 0.05 | 10.0 | 17.25 | 5.0 | 7.0 | 89.0 | 0.9 | 1.3 | 0.6 | 0.5 |
| 5 | 0.1 | 20.0 | 17.0 | 10.0 | 7.5 | 88.0 | 0.8 | 1.5 | 0.5 | 0.5 |
| 6 | 0.2 | 10.0 | 17.0 | 5.0 | 7.0 | 83.0 | 0.5 | 1.0 | 4.0 | 3.0 |

[a]Starting material analysis by liquid chromatography (area %).
C1 = 52.7 (1S,cis S and 1R,cis R mixture of cypermethrin isomers
C2 = 41.2 (1R,cis S and 1S,cis R mixture of cypermethrin isomers
T1 = 2.7 (1S,trans S and 1R,trans R mixture of cypermethrin isomers
T2 = 1.2 (1R,trans S and 1S,trans R mixture of cypermethrin isomers
Total benzoin isomers (B1 and B2) was approximately 2.2.

TABLE 2

Enantiomeric Enrichment of cis,trans-Cypermethrin Using 1,1,3,3-Tetramethylguanidine (TMG) in n-Heptane (solvent) at Room Temperature

| Experiment No. | TMG Amount (g) | Solvent Amount (g) | Reaction Time (Hr) | Starting Material[a] (g) | Product Analysis Liquid Chromatography-Area % | | | | | | | |
|---|---|---|---|---|---|---|---|---|---|---|---|---|
| | | | | | C1 | C2 | T1 | T2 | B2 | B2 | B3 | B4 |
| 7 | 0.1 | 20.0 | 20.0 | 10.0 | 11.0 | 35.0 | 10.0 | 39.0 | 1.2 | 0.8 | 0.9 | 0.6 |
| 8 | 0.05 | 20.0 | 20.0 | 10.0 | 21.0 | 25.0 | 24.0 | 27.0 | 0.5 | 0.3 | 0.4 | 0.2 |
| 9 | 0.05 | 20.0 | 26.0 | 10.0 | 9.0 | 36.0 | 10.0 | 38.0 | 1.4 | 0.6 | 1.0 | 0.6 |

[a]Starting material analysis by liquid chromatography (area %).
C1 = 28.0 (1S,cis S and 1R,cis R mixture of cypermethrin isomers
C2 = 21.0 (1R,cis S and 1S,cis R mixture of cypermethrin isomers
T1 = 29.4 (1S,trans S and 1R,trans R mixture of cypermethrin isomers
T2 = 20.8 (1R,trans S and 1S,trans R mixture of cypermethrin isomers
Total benzoin isomers (B1 and B2) was approximately 0.8.

I claim:

1. A process for producing a pesticidally more active isomer or mixture of isomers of a pyrethroid having an asymmetric carbon atom to which an epimerizable proton is attached from a pesticidally less active isomer or mixture of isomers of said pyrethroid, which consists essentially of:

(a) forming a stirrable slurry consisting essentially of (1) a less pesticidally active isomer or mixture of isomers of a pyrethroid having an asymmetric carbon atom to which an epimerizable proton is attached, (2) an aliphatic or alicyclic hydrocarbon of 5 to 16 carbon atoms in which the pesticidally more active isomer or mixture of isomers is substantially insoluble and the pesticidally less active isomer or mixture of isomers is relatively more soluble, said hydrocarbon being substantially saturated with the pesticidally more active isomer or mixture of isomers, and (3) an epimerization agent selected from the group consisting of 1,1,3,3-tetramethylguanidine and 1,8-diazabicyclo[5.4.0]undec-7-ene, wherein the amount of epimerization agent comprises from about 0.5–5.0 wt. percent, based on the weight of the pyrethroid starting material;

(b) agitating said slurry at a temperature in the range of 5° C. to 35° C. for a period of 2 to 24 hours; and (c) separating from said slurry a product substantially enriched with respect to the pesticidally more active isomer or mixture of isomers.

2. The process of claim 1, in which the epimerizable proton is attached to a carbon bearing a cyano group.

3. The process of claim 2, in which the pyrethroid is selected from cypermethrin and cyfluthrin.

4. The process of claim 3, in which the starting isomer comprises the four enantiomer pairs of cypetmethrin and the resulting product predominantly comprises the cis-2 and trans-2 isomer pairs thereof.

5. The process of claim 3, in which the starting isomer comprises the cis-1 and cis-2 enantiomer pair of cypermethrin and the resulting product predominantly comprises the cis-2 enantiomer pair thereof.

6. The process of claim 3, in which the starting mixture comprises the trans-1 and trans-2 enantiomer pairs of cypermethrin and the resulting product predominantly comprises the trans-2 enantiomer pair thereof.

7. The process of any of claims 1, 2, 3, 4, 5, or 6, in which said hydrocarbon is heptane.

8. The process of any of claims 1, 2, 3, 4, 5, or 6, in which the product is separated by neutralizing the epimerization agent, extracting the resulting neutralized reaction mixture with a solvent in which all isomers are soluble, then removing the solvent.

* * * * *